US009763717B2

United States Patent
Chiquillo Perez (10) Patent No.: US 9,763,717 B2
(45) Date of Patent: Sep. 19, 2017

(54) MULTI-TAPERED IMPLANT SCREW

(76) Inventor: Luis Mauricio Chiquillo Perez, Bogotá (CO)

( * ) Notice: Subject to any disclaimer, the term of this patent is extended or adjusted under 35 U.S.C. 154(b) by 0 days.

(21) Appl. No.: 13/582,699

(22) PCT Filed: Mar. 3, 2010

(86) PCT No.: PCT/IB2010/050924
§ 371 (c)(1),
(2), (4) Date: Nov. 20, 2012

(87) PCT Pub. No.: WO2011/107829
PCT Pub. Date: Sep. 9, 2011

(65) Prior Publication Data
US 2013/0090696 A1 Apr. 11, 2013

(51) Int. Cl.
*A61C 8/00* (2006.01)
*A61B 17/86* (2006.01)
(52) U.S. Cl.
CPC ............ *A61B 17/86* (2013.01); *A61C 8/0022* (2013.01)
(58) Field of Classification Search
CPC ... A61C 8/0037; A61C 8/0045; A61C 8/0022; A61B 17/86
USPC .................................................. 433/172–176
See application file for complete search history.

(56) References Cited

U.S. PATENT DOCUMENTS

| 5,527,183 | A | 6/1996 | O'Brien |
| 5,766,263 | A * | 6/1998 | Grundei et al. ............ 623/23.15 |
| 6,030,162 | A * | 2/2000 | Huebner ........................ 411/413 |
| 7,240,542 | B2 | 7/2007 | Gustafsson et al. |
| D603,513 | S | 11/2009 | Emanuelli |
| 2007/0037123 | A1 | 2/2007 | Mansueto et al. |
| 2008/0234758 | A1* | 9/2008 | Fisher et al. ................... 606/309 |
| 2008/0241791 | A1 | 10/2008 | Bulard et al. |
| 2010/0009316 | A1* | 1/2010 | Hurson ........................ 433/173 |
| 2011/0045437 | A1* | 2/2011 | Arni .............................. 433/174 |
| 2011/0195380 | A1* | 8/2011 | Giorno ......................... 433/174 |

FOREIGN PATENT DOCUMENTS

| EP | 1 416 872 | 4/2008 |
| FR | 2 942 952 | 9/2010 |

OTHER PUBLICATIONS

International Search Report for International Application No. PCT/IB2010/050924 mailed Nov. 30, 2010.

* cited by examiner

*Primary Examiner* — Heidi M Eide
(74) *Attorney, Agent, or Firm* — Hoglund & Pamias, PSC; Roberto J. Rios (57) ABSTRACT

The present invention relates to a screw suitable for being implanted inside a bone, characterized in that said screw comprises two to four inverted cones along the longitudinal axis thereof, where the narrowest tip of the bottom cone corresponds to the bottom tip of the screw and where the height of each one of the cones at either end of the screw is between 20% and 80% of the total length of the screw, ensuring better acceptance, adaptation and osseous integration, and reducing trauma due to the pressure the implant exerts on the bone when the screw is fully tightened, minimizing reabsorption and, thus, producing more aesthetically pleasing results.

26 Claims, 12 Drawing Sheets
(7 of 12 Drawing Sheet(s) Filed in Color)

MULTI-TAPERED IMPLANT SCREW

This application is a National Stage Application of PCT/IB2010/050924, filed 3 Mar. 2010, and which application is incorporated herein by reference. To the extent appropriate, a claim of priority is made to the above disclosed application.

The present invention refers to a screw to be implanted inside a bone characterized by comprising from to four inverted cones along its longitudinal axis, wherein the narrowest end of the lower cone corresponds to the lower end of the screw and wherein the height of each cone in the ends of the screw is between 20 and 80% of the total length of the screw, whereby a better acceptance, adaptation, bone integration is achieved, the trauma caused by the pressure exerted by the implant on the bone at the time of its final torque is reduced, reabsorption is minimized and thus, better aesthetic results are produced.

In a first embodiment, the screw comprises two inverted cones along its longitudinal axis, which ends being narrower than the central part of the screw body and said narrower ends matching with the upper and lower ends of the screw. In another alternative of the invention, the screw comprises three cones wherein the narrowest end of the second cone is attached to the narrowest end of the third cone, which narrowest end matches with the upper end of the screw.

In a last preferred embodiment of the invention, the screw comprises four cones forming a sandglass shaped screw, wherein the widest end of the third cone is attached to the widest end of the fourth cone, such that the narrowest ends of the first and fourth cones correspond to the upper and lower ends of the screw.

BACKGROUND OF THE INVENTION

In general, body implants such as dental screws are surgically inserted in the bones of a patient, such in the jaw, wherein the implant is integrated to the bone. In the field of dentistry, implants to be screwed or pressed inside a cavity perforated in the bone are well known.

Actually, one of the greatest challenges in piezoelectric surgery is based on correctly expanding the bone tables in important defects and knife edges in order to allow the correct location of an implant, to maintain the architecture and the bone function thereby guaranteeing the functional and aesthetic rehabilitation.

Unfortunately, up to date the traditional techniques disclosed in the literature just refer to the sandwich technique which was initiated by maxillofacial surgeons more than 20 years ago by using saws for the separation of bone tables which generally originates a great loss of bone tissue in the zone where the implant is done. Other techniques have tried to use the insertion of internal and external auto-grafts (known in the technical field as on-lay and in-lay), which besides of being complex, is traumatic and the results basically depend on the skill, preparation and expertise of the surgeon. However, many of the problems related with bone insufficiency can be solved through more conservative techniques.

From year 2000, when Tommaso Verselloti dabbled with the concept of piezo-surgery in the field of dentistry using inserts which allow to make fine cuts in narrower bone tables, the technique known as sandwich technique took great relevance again. Such technique requires of some vestibular bone relaxants which allow to expand the tissue for the location of the bone graft and thus guaranteeing the stability thereof with optimal quality. However, the immediate location of implants in bone cortical less than 2 mm of calibration in the peak area is counterproductive due to the fact that four problems are generated:
    Wrong positioning of the implants,
    Secondary slope of the implants,
    Fracture of the weakest cortical area in the maxillary vestibular and in the maxillary lingual; and
    Reabsorption of the bone cortical area with the consequent exposure of implant threads and aesthetic defects due to such exposure.

Although with the prior technique it was possible to successfully expand the bone tables, depending on the type of defect, common implants do not stay in the optimal position for an aesthetic rehabilitation requiring thereby known castable abutments (widely known as "UCLA" type abutments) for correcting wrong positions, and even in extreme cases it is necessary to remove the implant. These results were mainly caused by not understanding the ways of trabecular bone to make the internal bone cuts whether they are vertical, horizontal and oblique.

In addition, in many cases it can be seen that during the expansion and further location of the implants in the correct position, after one month such implants are in different positions to the original ones, mainly distally and mesially, which is mainly caused by the vestibular relaxants made to achieve the expansion of the bone tables. These implant movements are commonly known as secondary tilt and have been associated with the non-controlled bone expansion.

In addition to the above, the implants found in the state of the art also represented the problem of the cortical fracture, due to the pressure generated by the implant in the peak area caused by the cylindrical design used before the present invention. Such design generates a loss of continuity of the bone tissue vertically with some variations during the placing of the implant in the final stage, i.e. when the closing laps of the thread are being introduced.

Likewise, the absorption of the bone cortical area generated by the loss of bone tissue vertically has been disclosed, which is caused by the pressure generated by the expanders. The only solution detected for such problem is to make bone integration, but the aesthetic results produced were undesirable.

Accordingly, one of the greatest challenges is to make the bone expansion and to avoid such inconvenient. In order to improve the achievements done with the cylindrical implants the screws for implants of the present invention have been developed characterized in that its body is a threaded cylinder and one of its ends is tapered for facilitating the introduction of the screw in the bone. One of such type of screws can be found in the industrial design U.S. D603,513, which discloses a screw being formed by a cylindrical body covered by a thread system wherein the gap between threads is the same, a threaded and tapered end and a flat upper area having inside a tapered seat and an hexagonal space, in which the attachment or inner abutment and notches located parallel to the longitudinal axis of the screw in the lower part thereof are adjusted.

There has also been an effort in improving the shape of the threads located on the screws and as disclosed in application U.S. 2008/0241791, which discloses a dental implant having a body with blunt threads and other sharp edges in order to help forming a thread inside the bone to the perforated.

Similarly, document U.S. Pat. No. 7,240,542 discloses implants showing cylindrical screws with an apical and a coronal end. Such screw is slanted in the upper or coronal part in a determined angle in order that the implant accommodates to the jaw bone anatomy of the patient. The implant in its longitudinal configuration is funnel shaped wherein the diameter decreases from the upper part to become smaller in the lower part. In addition, this design shows that the upper part has a thread with gaps, between each thread, less than the space between the threads in the lower part.

On the other hand, patent EP 1416872 teaches a screw to be inserted in the bone wherein the upper part of the screw shows a thread with a gap smaller than the space for the thread in the lower part thereof. In addition, such patent shows that the coronal part (upper part of the implant) has an axial length such that when the implant is installed, the configuration of such portion is confined with the bone cortical tissue layer of the patient, due to a tapered configuration of no more than 5° with respect to the external surface of the lower part of the screw.

U.S. Pat. No. 5,527,183 discloses an orthopedic implant having a coronal end, a distal end and a plurality of segments, namely four in the upper part of the implant and the lower part having a finer thread, i.e. with a smaller gap compared to the one showed for the four segments in the upper part.

Actually the closest document in the state of the art to the present invention is formed by a screw commercially available under the trademark Nobelactive from Nobelbiocare, which is characterized by having a tapered and threaded body and an inverted cone shaped coronal region, which length does exceed 10% of the total length of the screw and according to the manufacturer, it is useful for increasing the alveolar bone volume around the implant. Despite having the above indicated feature, such implants do not avoid the fractures of the bone crest, the tilts of the implant and the bone reabsorption of bony ridges less than 3 mm.

In view of the above cited information it is clear that there was a need in the state of art which had not been fulfilled for providing a screw which avoids the inconvenient associated to the secondary tilt, fracture of the bone cortical and its reabsorption, achieving a greater irrigation of the bone tissues.

The inventor surprisingly found that the reduction of the upper and lower ends of the screw, specially so the upper cone has a length between 20% and 80% of the total length of the screw, creating a double cone which allows to reduce the pressure exerted by the traditional implant on the bone releases tensions, minimizing thereby the risk of vertical fractures and avoiding the process of bone reabsorption and therefore, avoiding problems usually related with implantation processes, such as periimplantitis and loss of support tissue, with the subsequent loss of implant.

In addition to the above, with the novel double tapered shape of the screw for implant disclosed herein, the screw exerts less pressure on the expanded bone tissue, does not generate secondary tilt, allows an excellent apical fixation guaranteeing bone integration and producing less trauma on the patient minimizing thereby pain and inflammation produced by the expansion of the bone. Likewise, the extra-oral implants with double cone could be used for rehabilitation with better prognosis and better durability in the patient than cylindrical implants.

DETAILED DESCRIPTION OF THE DRAWINGS

The patent or application file contains at least one figure executed as a color photograph. Copies of this patent or patent application publication with color photograph(s) will be provided by the Office upon request and payment of the necessary fee.

DETAILED DESCRIPTION OF THE INVENTION

The present invention refers to a screw (1) for implants showing multiple cones along its longitudinal axis (L), namely the screw (1) for implants is characterized by comprising between two and four cones, wherein the narrowest end of the lower cone (41) corresponds to the lower end of the screw (4) and the other cones are joined to the lower cone (41) or to each other, such that there is a match between the widest end of a cone and the widest end of the adjacent cone and the narrowest end of a cone with the narrowest end of the adjacent cone and wherein the length of each cone located on the ends of the screw is between 20% and 80% of the total length of the screw.

In a first embodiment of the invention, the screw is a double tapered screw, the greatest diameter (2) is located in the central area of the screw and matches or not with the center thereof. From such diameter (2) the external surface is tilted with respect to the longitudinal axis (L) in equal or different angles progressively decreasing its diameter towards the upper (3) and lower (4) ends.

Figure 1A:
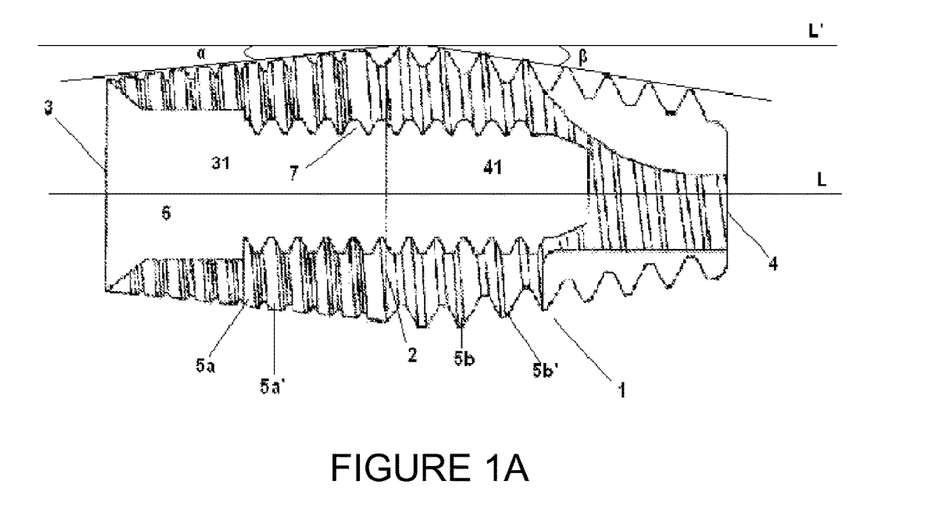
FIG. 1A. Cross section of a double tapered screw according to the invention wherein the greatest diameter (2) is located exactly in the center thereof and its tilt angle with respect to the longitudinal axis in the upper part is equal to the tilt angle of the lower part.
Figure 1B:
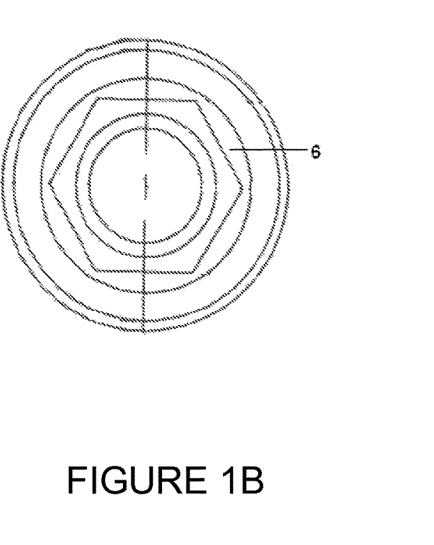
FIG. 1B. Upper view of the double tapered screw of the invention wherein the inner connection of the screw has hexagonal lock.
Figure 2A:
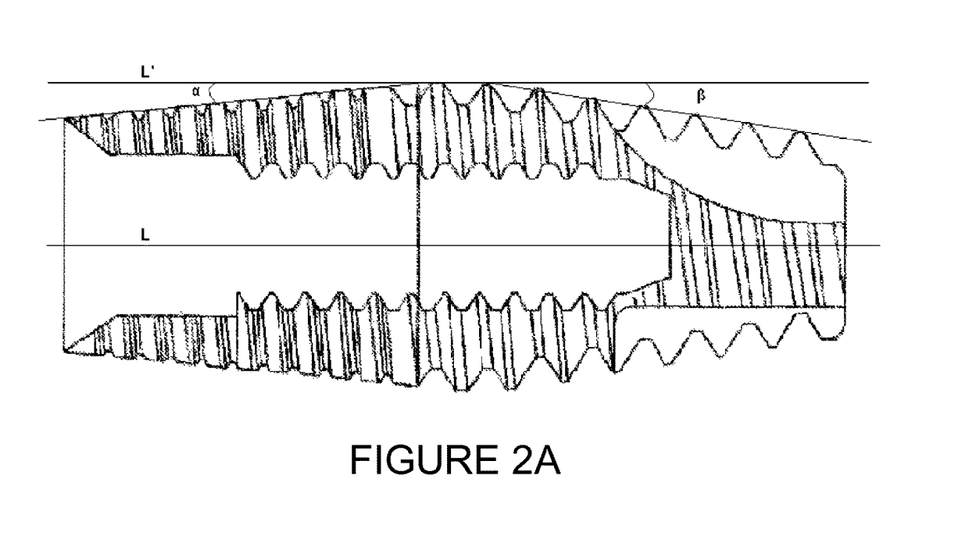
FIG. 2A. Cross section of a double tapered screw according to the invention wherein the greatest diameter (2) is located exactly in the center thereof and the angle tilt $\alpha$ is less than the angle tilt $\beta$.
Figure 2B:
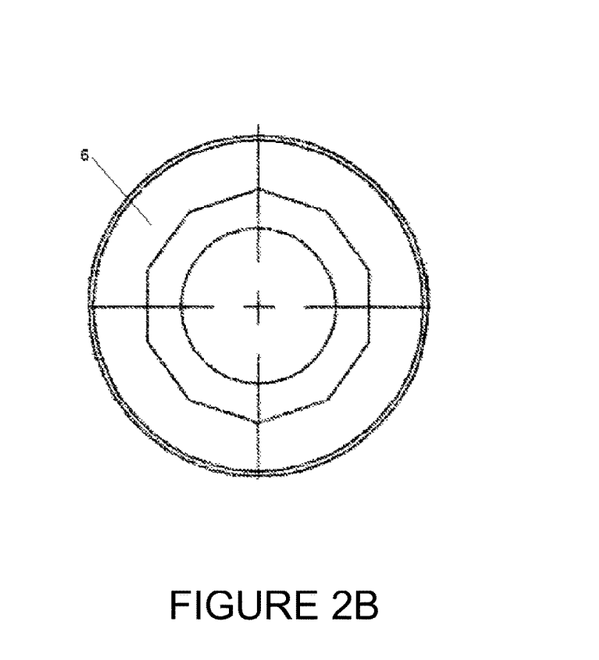
FIG. 2B. Upper view of the double tapered screw of the invention wherein the internal connection of the screw has decagonal lock.

The above mentioned tilts create two cones, an upper cone (31) and a lower cone (41) exhibiting a common base which corresponds to the greatest diameter (2) and which length is between 20% and 80% of the total length of the screw. Thus, such greatest diameter (2) can match with the center of the screw (1), i.e., symmetrically, as shown in FIG. 1, or can be located on a different spot between the center and one of the ends as shown in FIG. 2, provided that the distance between either end (3, 4) and the greatest diameter (2) is between 20% and 80% of the total length of the screw (1). Preferably, the greatest diameter (2) is located on a spot between half the distance existing between the upper end (3) and the center and half the distance existing between the lower end (4) and the center.

Figure 5:
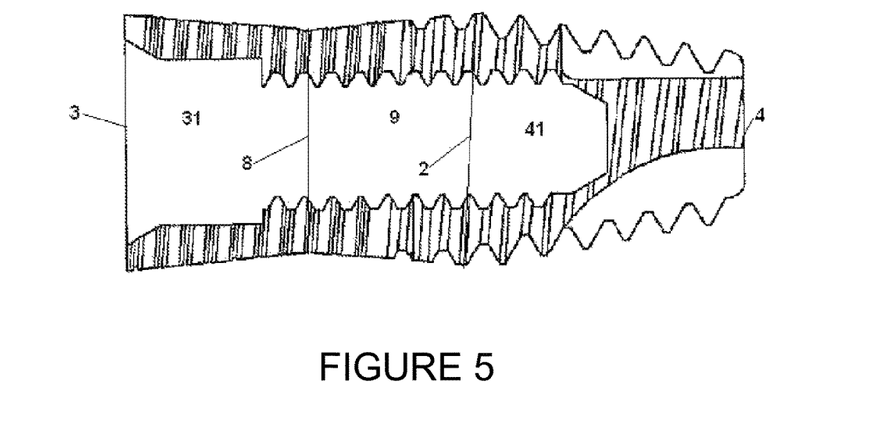
FIG. 5. Cross section of a screw with three cones, wherein the narrowest end of the lower cone corresponds to the lower end of the screw, the join of its widest ends form the greatest diameter (2) and the join of the second and third cones form the waist (8).

In another alternative of the invention shown in FIG. 5, which shows a screw (1) comprising three cones (31, 9, 41). The cone (31) located in the upper end of the screw (1) such that the widest end of such cone (31) corresponds to the end (3) of the screw and the opposite end matches with the narrowest end of the second cone (9) forming the waist (8) of the screw (1), and the widest end of the second central cone (9) is joined to the widest end of the third cone (41) wherein the greatest diameter (2) is formed, and such cone also has a narrow end which corresponds to the upper end (4) of the screw (1).

Figure 6:
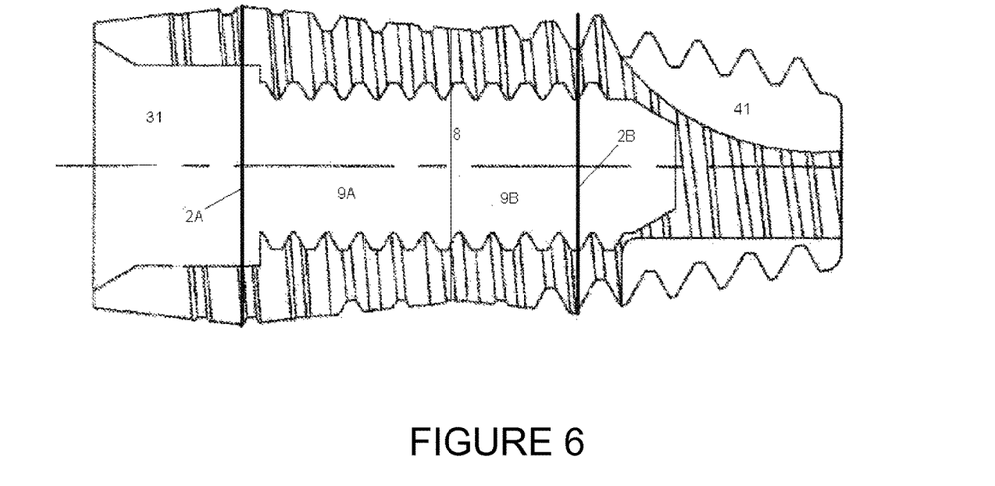
FIG. 6. Cross section of a four tapered screw forming a sandglass shaped screw, wherein the narrowest ends of two cones correspond to the ends of the screw, the join of its widest ends form two greatest diameters (2A and 2B) and in the central part of the screw the narrowest ends of the two central cones are joined creating thereby a waist (8).
Figure 7:
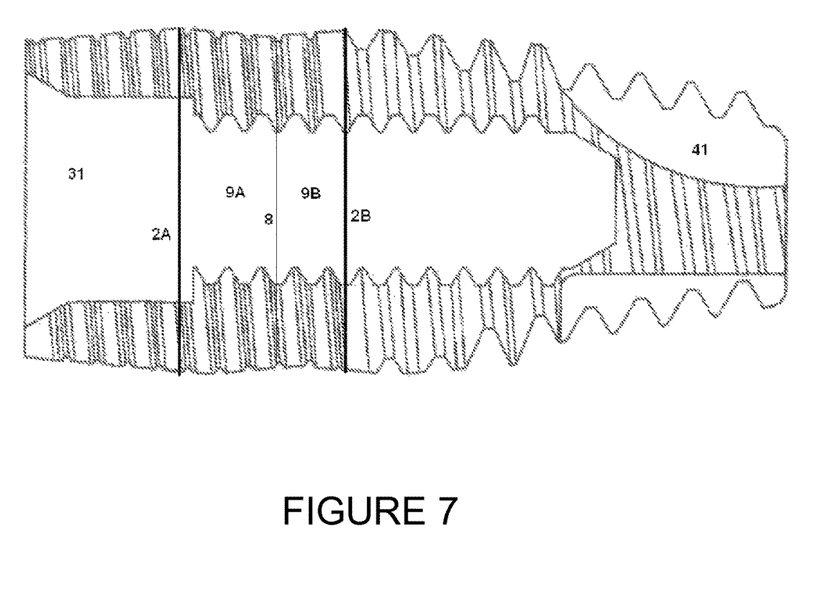
FIG. 7. Cross section of a four tapered screw forming a sandglass shaped screw, wherein the join of the narrower ends of the two central cones, i.e. the waist (8) do not match with the center of the screw.

A third preferred embodiment of the invention is shown in FIGS. 6 and 7. Therein the screw (1) comprises four cones creating a screw with two cones located in the ends of the screw (31, 41) and two central cones (9A, 9B). Cone (31) is located in the upper end of the screw (1) such that the narrowest end of such cone (31) corresponds to the end (3) of the screw and the opposite end matches with the widest end of the second cone (9A) creating thereby a first greatest diameter (2A), such central cone (9A) is joined to the narrowest end of the third cone (9B), forming the waist (8) of the screw (1), the widest end of the second central cone (9B) matches with the widest end of the fourth cone (41) wherein the second greatest diameter (2B) is formed, and it also has a narrow end which corresponds to the upper end (4) of the screw (1).

The arithmetic difference between the greatest diameter(s) (2) and the diameter of each of the ends (3, 4) or the waist (8) is given by the tilt of the surface of each cone (31, 9, 9A, 9B, 41). The tilt of the cones (31, 9, 9A, 9B, 41) is determined by two imaginary angles α and β formed between a line L', parallel to the longitudinal axis L and tangent to the screw at the height of the same or the greatest diameter(s) (2), and the external surface of said cones (31, 9, 9A, 9B, 41).

Figure 3:
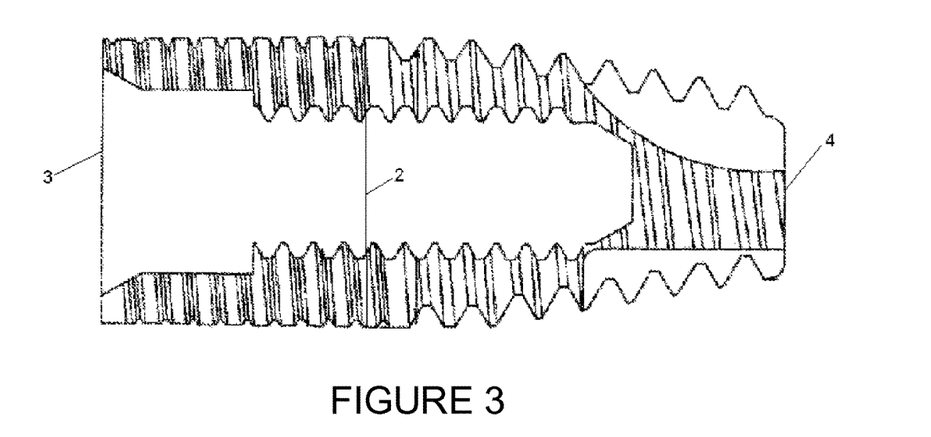
FIG. 3. Cross section of a double tapered screw according to the invention wherein the greatest diameter (2) is located to the upper half of the screw and the angle tilt $\alpha$ is less than the angle tilt $\beta$.
Figure 4:
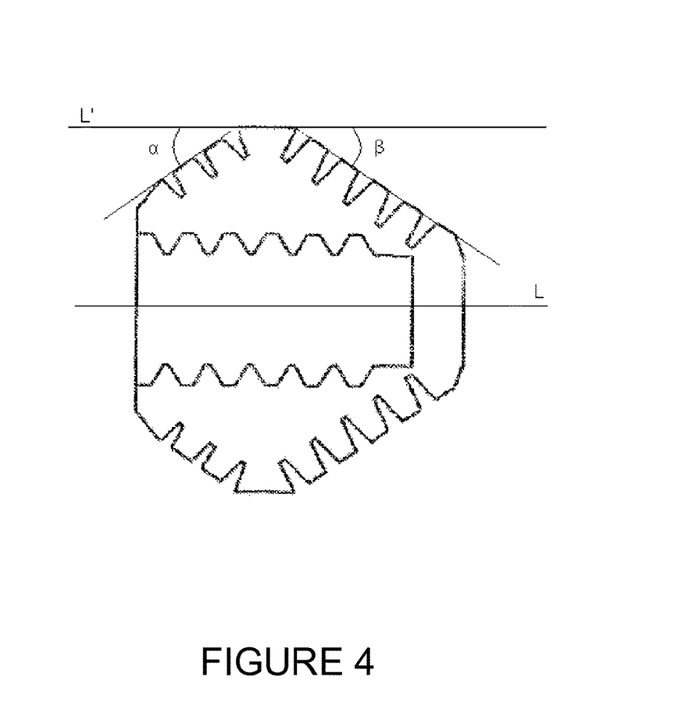
FIG. 4. Cross section of a double tapered screw according to the invention wherein the widest part of the screw is located in the central part of the implant and the tilt of angles $\alpha$ and $\beta$ with respect to the longitudinal axis L' is 45°.

The amplitude of the angles α and β ranges between 0.5° and 60°. FIGS. 1 to 3 represent screws for dentistry use, which angles α and β are between 0.5° and 20°. In a preferred alternative, the amplitude of angles α and β is between 1° and 10°. In another embodiment of the invention, the implants are extraoral and angles α and β are between 0.5° and 60°, preferably 45°, as shown in FIG. 4.

Cones (31, 9, 9A, 9B, 41) exhibit on its surface a threaded pitch (5). The average distance between each thread ranges between 0.1 mm and 2.5 mm. The distance between thread (5a) and thread (5a') of the threaded pitch of the upper area surface of the screw, which covers from the upper end (3) to the 45% of the length of the screw as measured from said upper end (3), is less than the distance between thread (5b) and thread (5b') of the threaded pitch of the lower area surface of the screw, which covers from the lower end (4) to the 80% of the length of the screw as measured from said lower end (4). Preferably, the distance between thread (5a) and thread (5a') of the threaded pitch of the upper area surface of the screw ranges between 0.1 mm and 0.5 mm, while the distance between thread (5b) and thread (5b') of the threaded pitch of the upper area surface of the screw ranges between 0.3 mm and 2.5 mm.

Figure 8:
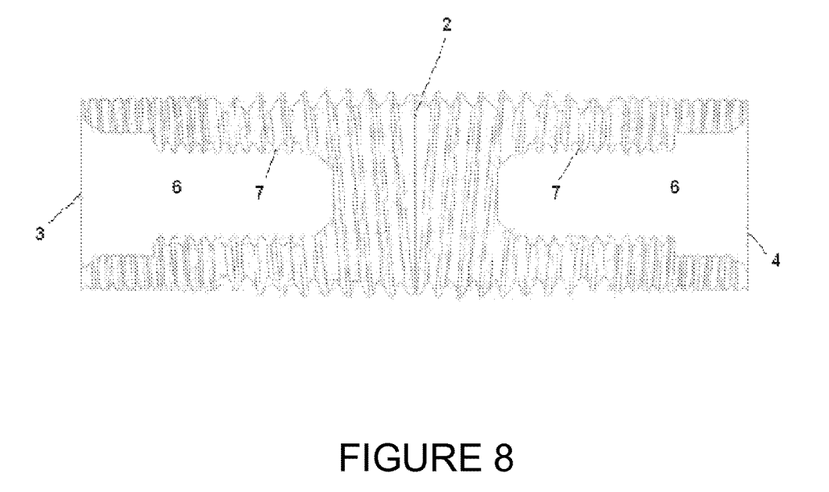
FIG. 8. Cross section of a double cone screw according to the invention which comprises two internal spaces for introducing two attachments or abutments allowing the joining of two bones.

Said screw (1) comprises a platform formed by an internal gap (6) which has a threaded pitch (7), which allows the introduction of a through screw which will fix the body of the attachment or abutment, and has a bottom with shape as a polygon of 6 to 12 sides, which locks the attachment or abutment by fixing it in a determined position. The entrance to such gap (6) is made through the upper end (3). In another alternative of the invention, the screw (1) comprises two opposite internal spaces, wherein the entrance to each of said spaces matches with the ends (3, 4) of the screw (1), enabling thereby the fixation of two attachments (abutments), each on an end (3, 4), as shown in FIG. 8.

Optionally, the screw of the present invention may also have notches disposed on the end of the cone (41) located in the same direction as the longitudinal axis of the screw. The screw may have between 1 to 4 notches symmetrically disposed on the surface of the cone (41).

The screw according to the present invention has a distance from the end (3) to the end (4) from 6.0 mm to 120.0 mm and the greatest diameter (2) is between 2.0 and 10.0 mm.

Preferably, the screw of the present invention may be manufactured in a material selected from the group consisting of titanium, zirconium, chrome, cobalt and alloys thereof.

EXAMPLES

Example 1

Figure 9A:
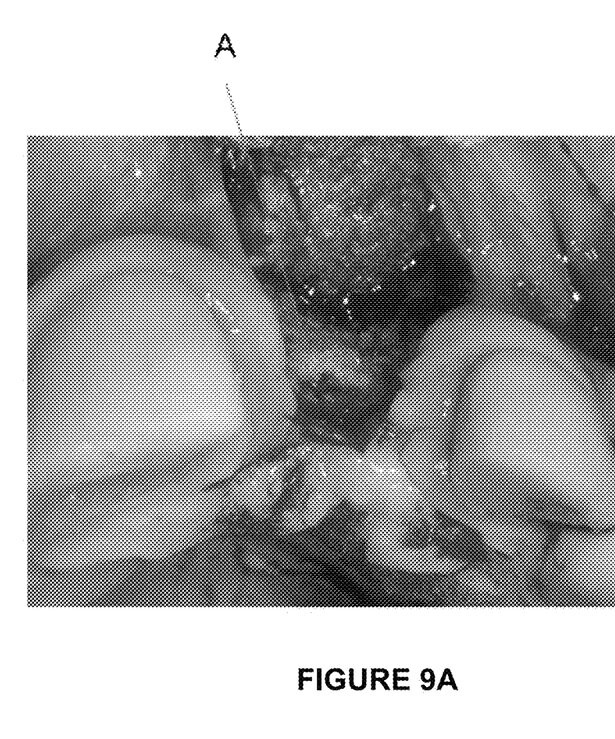
FIG. 9A shows a photograph of a patient with a flange of 2 mm thick in which an implant will be introduced using the screw, according to the present invention.
Figure 9B:
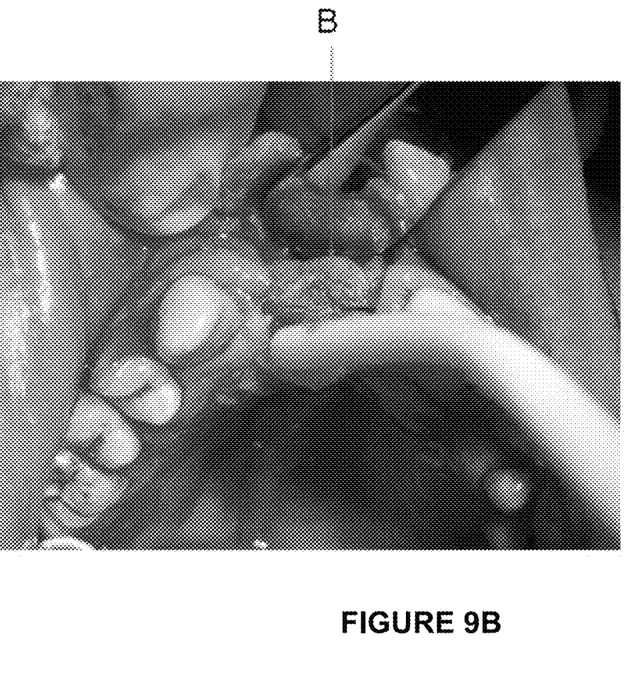
FIG. 9B shows another photograph of a patient with a flange of 3 mm thick in which an implant is introduced using an inverted cone screw, disclosed in the state of the art.

In order to demonstrate the beneficial and unexpected effects obtained with the screws of the present invention, especially in complicated cases wherein the ridge has less than 3 mm, two patients were treated with the same bone expansion and implant insertion process. The photograph of the first one, is shown in FIG. 9A) where it can be seen that the patient has a ridge of less than 2 mm thick. In this patient, who represents increased risk for showing the typical problems of implants due to the small ridge, the multi-tapered implant of the present invention will be used. Photograph 9B represents a shot prior to the installation of the implant, wherein it can be seen that the ridge is 3 mm thick, which facilitates the installation of the implant. In this patient the inverted cone implant as disclosed in the closest state of the art can be used. In both cases the maximum diameter of the screws evaluated is 3.5 mm.

Figure 10A:
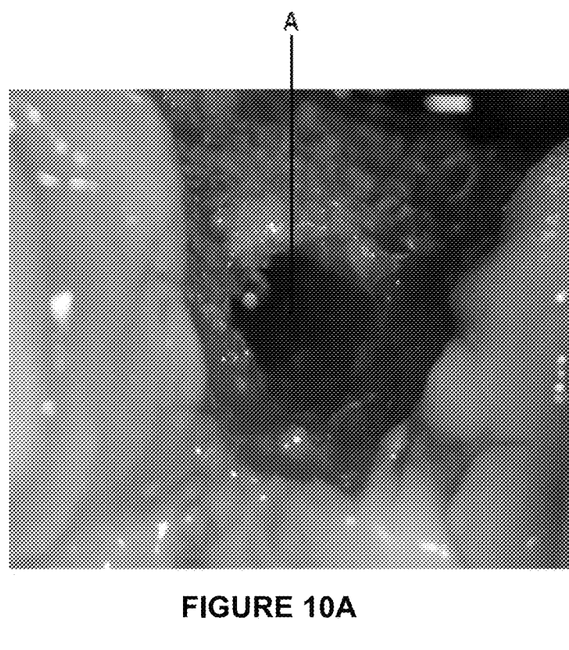
FIG. 10A. Shows a photograph of the surgical alveolus with no fracture and ready to receive the implant using the screw of the present invention.
Figure 10B:
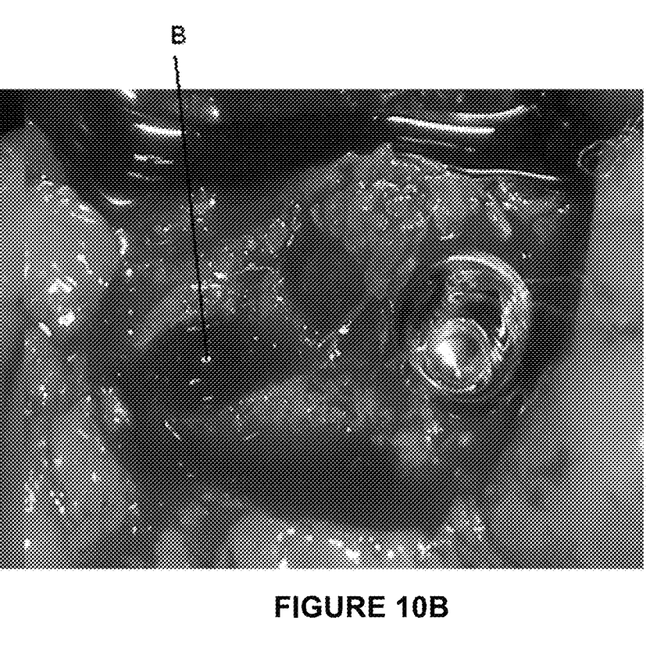
FIG. 10B. Shows a photograph of the surgical alveolus with no fracture and ready to receive the implant using the inverted cone screw, disclosed in the state of the art.

The bone expansion is then made in order to create an alveolus in each patient. FIGS. 10A and 10B show the alveolus without fractures and ready to receive the respective implant.

Figure 11A:
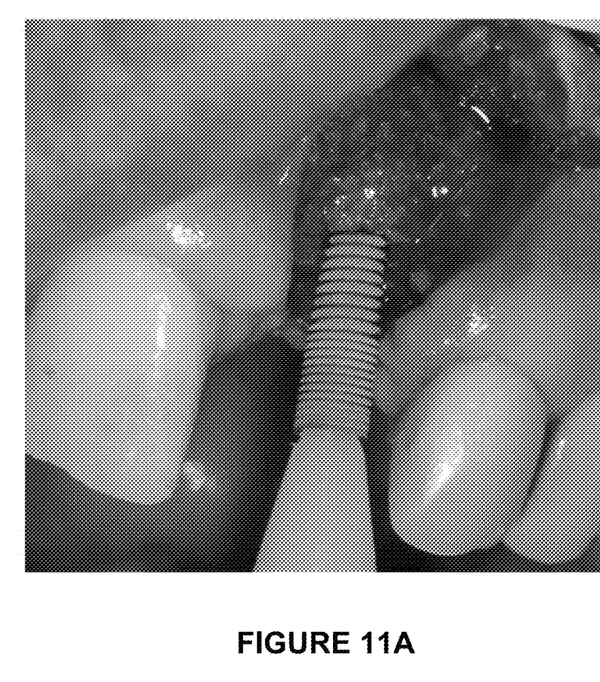
FIG. 11A. Shows a photograph during the installation process of the screw of the present invention.
Figure 11B:
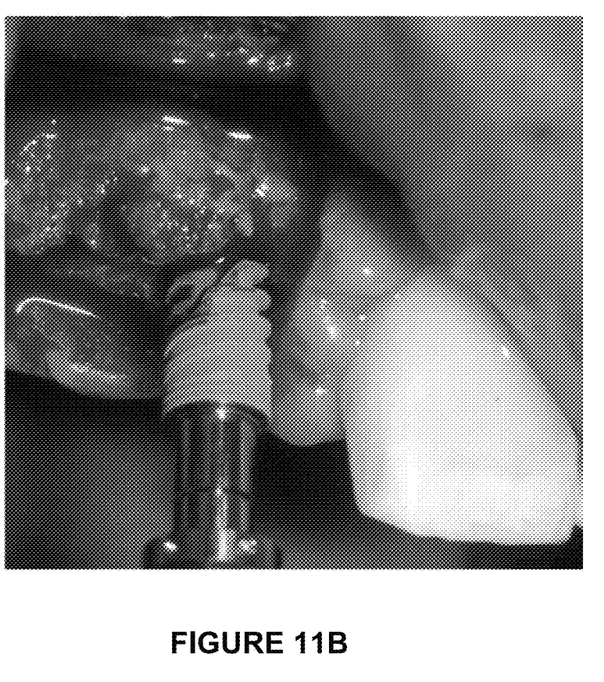
FIG. 11B. Shows a photograph during the installation process of the inverted cone screw, disclosed in the state of the art.

Afterwards, the installation of the implant of the present invention is started, which is shown in FIG. 11A, while FIG. 11B shows the installation process of the inverted cone implant existing in the state of the art. FIG. 11A shows that in the center of the screw (1) the cone is reduced, favoring thereby the integration of the bone implant and avoiding fractures, while FIG. 11B shows that the inverted region of the inverted cone screw is minimal and conicity is limited to the coronal area, affecting the integration of the bone implant and producing fractures.

In addition to the above, there is an undesirable effect associated to the gap existing between threads of the threaded pitch of the state of the art, which is distant and hampers the introduction of the screw, which also requires increased strength and pressure exerted on the bone. The use of the screws of the present invention also has allowed to establish that when using two types of threads, a wider and deeper threaded pitch in the apical area and one less thick in the coronal and central area an excellent primary fixation is achieves, which avoids dental wrong positions and secondary tilts.

In addition to the above, it has been seen that in some cases showing a sandglass shaped bone ridge, an implant having the woman shape to perfectly fit with the modifying surrounding expansion would also be required, requiring thereby a multi-tapered implant, which exhibit an equator and two tropics, wherein its conicity changes. This would avoid fenestrations, i.e. bone reabsorption in the vestibule middle part with its consequent translucency and aesthetic effects.

Figure 12A:
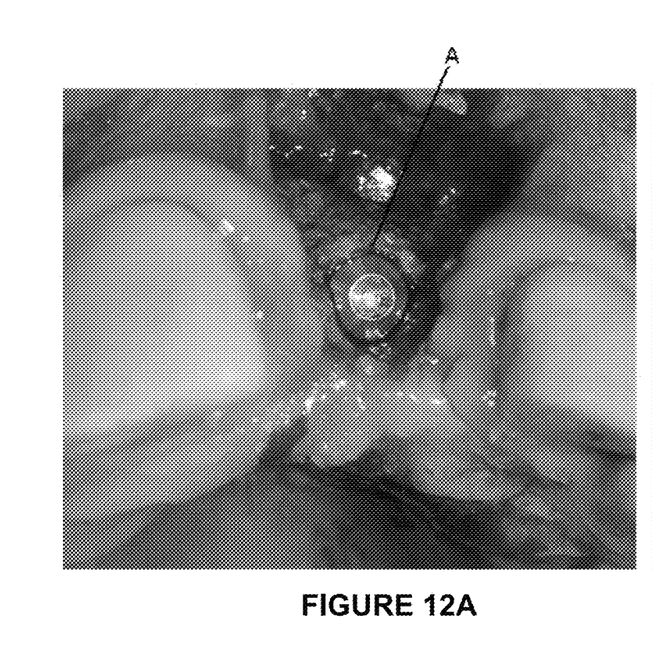
FIG. 12. Shows a comparison of the implant made with the screw of the present invention in its final position and the implant made with the inverted cone screw as disclosed in the state of the art in its final position.
Figure 12B:
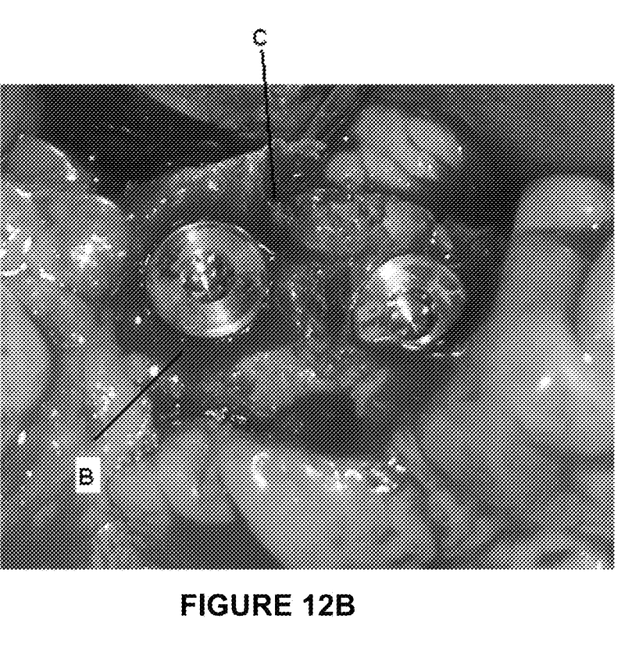
Figure 13:
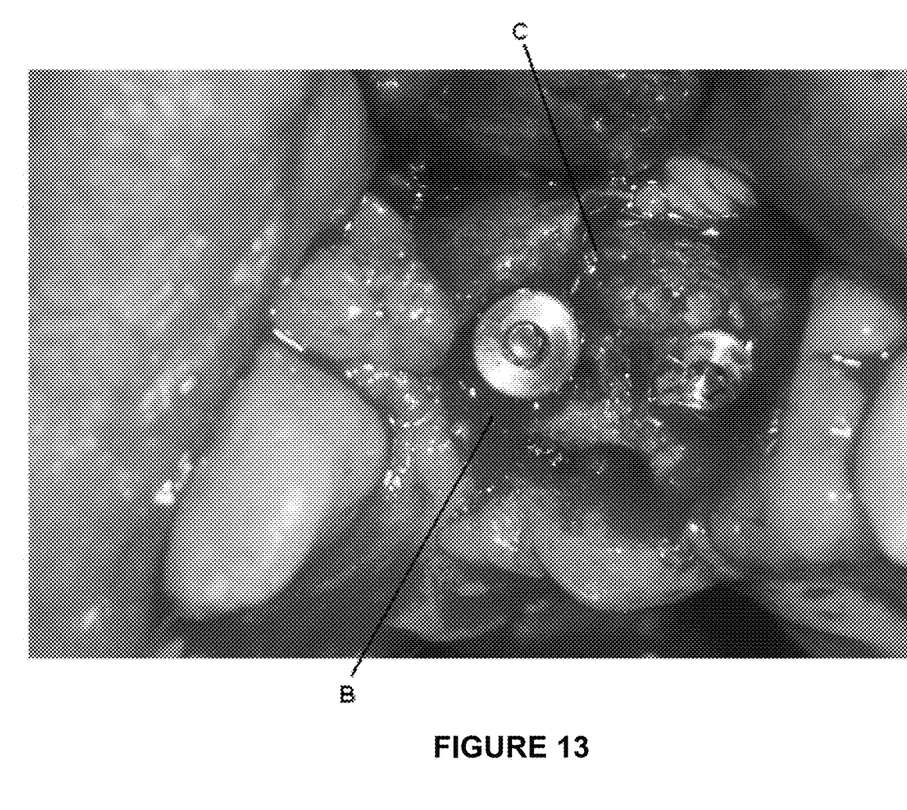
FIG. 13. Shows a detailed photograph of the implant made with the inverted cone screw, disclosed in the state of the art, and the effects thereof on the vestibule fracture and the crest.

FIG. 12 shows the definite position of the implants and allows to make a comparison between the results obtained with the implant (12A) of the present invention and those achieved with the implant (12B) of the state of the art. Letter A located on FIG. 12A) shows how the critical vestibule area is fractures free and the coronal support has been complete around the implant of the present invention. On the contrary, letter B on FIG. 12B) shows how the support of the inverted cone implant in the crest area has not been completely achieved, showing a gap between the bone and the screw and letter C shows the vestibule bone fracture, which leads to the bone reabsorption and possible exposure of the threads of the implant which would generate diseases and conditions in the patient such as periimplantitis. FIG. 13 shows in detail such effects, allowing thereby to clearly visualize the vestibule fracture and the lack of crest support.

Example 2

Figure 14:
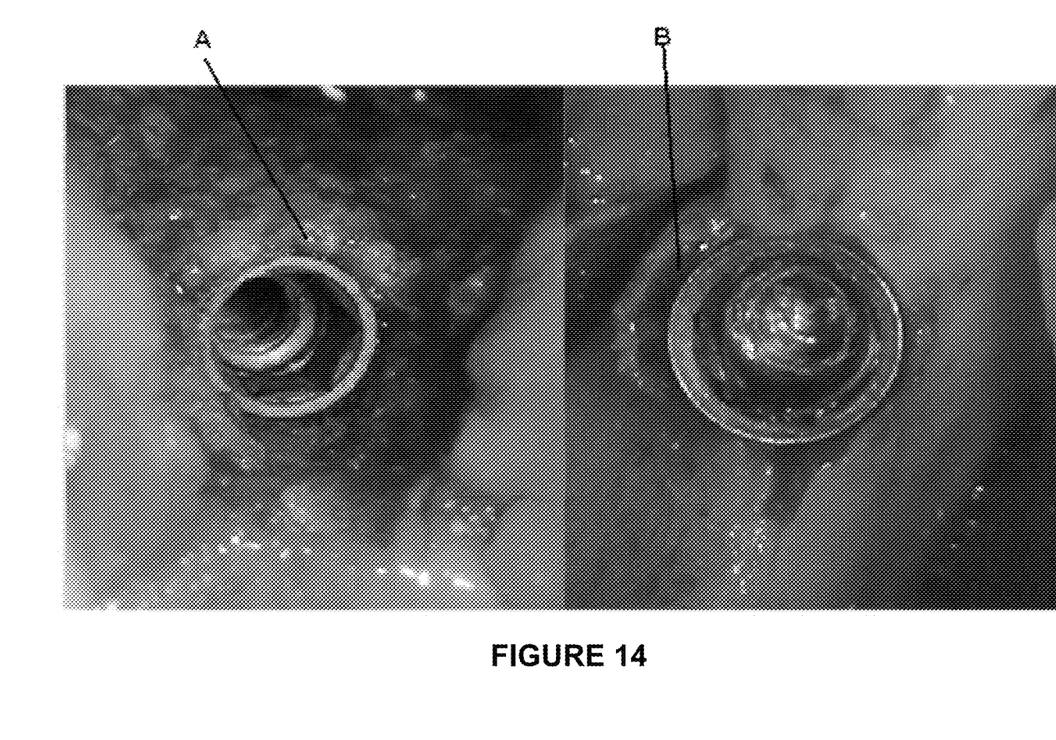
FIG. 14. Shows a comparison between the screw of the present invention and a conventional screw once it has been installed.

The same experiment was made comparing the results achieved with the screws of the present invention and the ones obtained through the use of cylindrical screws, widely known in the state of the art. FIG. 14 shows a comparison between the screw of the present invention and a conventional screw once these have been installed. As it can be appreciated, while the patient with the screw of the present invention does not exhibit any fracture and has achieved a total crest support around it, the patient with the conventional implant installed exhibits a notorious fracture, indicated on the figure with letter B.

Figure 15:
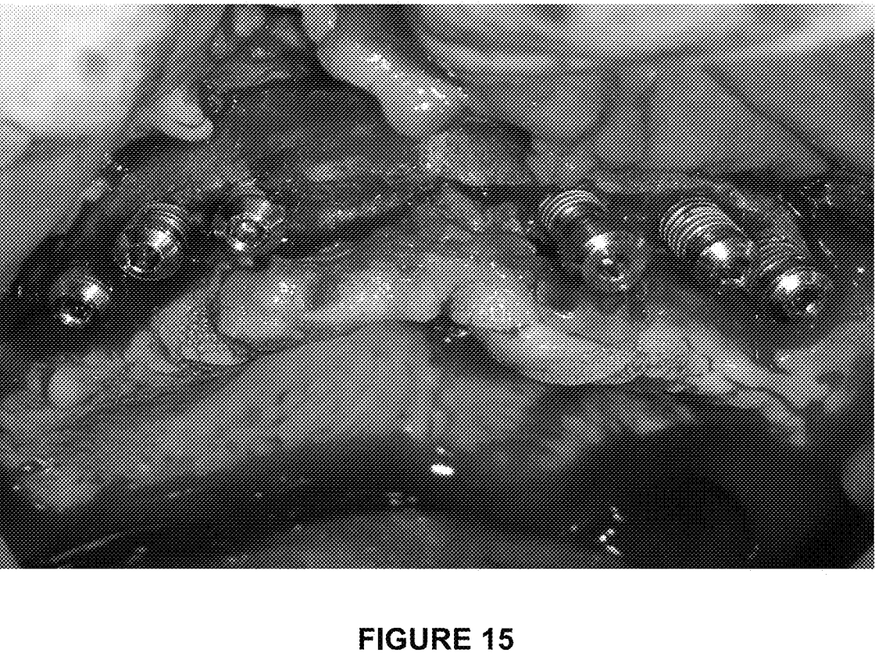
FIG. 15. Shows a photograph of conventional implants wherein it can be seen the reabsorption of the bone cortical area with the subsequent exposure of threads of the implant.

Moreover, FIG. 15 shows a photograph of conventional implants wherein it can be seen the reabsorption of the bone cortical area with the subsequent exposure of implant threads.

Considering the above data, the advantages of a multi-tapered implant versus an inverted cone implant are summarized as follow:

Adhesion

Multiple conicity occupies a great percentage of the implant, which allows the bone tissue to adhere in a better way to the implant once the expansion has been done and it has been properly placed. By progressively reducing the diameter in a length wider than the inverted cone, the screw of the present invention can avoid the fracture of the bone crest which is more feasible to happen with inverted cone screws such as those commercially available.

Absolut Crest Integration

Another advantage of the screw of the present invention is to avoid the fracture found in the crest when the implant enters the surgical alveolus, guaranteeing thereby that no further fenestrations will be produced, reducing the loss of bone and bone integration in the crest.

Minimum Crest Tension

From the operative point of view, another advantage is that the multiple conicity generates a minimum tension once the implant passes the equator on the surgical alveolus decreasing the adverse effects such as fractures and releasing tension on the surface area, while the inverted cone maintains the crest tension until the end of the installation of the implant.

Does not Generate Further Tilt of the Implant

Multiple conicity guarantees the stability of the implant in the position where it was located, eliminating thereby the annoying changes of position and tilt of the implant, caused by bone resilience and its adaptability once the implant has been installed.

Integration in Sandglass Areas

The modification of the screw so as to have multiple conicity allows that when there are sandglass shaped bone areas no fracture is produced in any segment of the surgical alveolus, which cannot be achieved with an inverted cone.

Smoother Threaded Pitch in the Coronal Area

The bone coronal area is extremely thin and delicate, thereby when doing the surgical alveolus caution must be taken so as to avoid a fracture in order to avoid a lack of continuity which would limit the bone irrigation and nutrition. The multi-tapered implant facilitates the access of the implant preserving the bone tables due to its smooth threaded pitch, which is not greater than 0.3 in the coronal tapered area. Unlike the present invention, the inverted cone has two different threaded pitches, a smooth one of 1 mm length maximum and another one with rough threaded pitch, both wide and deep which makes it aggressive promoting the bone fracture at the moment of the insertion of the implant to the surgical alveolus with the above mentioned consequences: fracture and lack of support.

The invention claimed is:

1. A multi-frustum screw for dental implants comprising: three threaded frustums, the threaded frustums selected from a coronal frustum forming an upper end of the screw, an apical frustum forming a lower end of the screw, and a central frustum positioned between the coronal frustum and the apical frustum, wherein the coronal frustum, the central frustum, and the apical frustum have a common longitudinal axis, said screw has a first inner base formed by an internal gap provided on said upper end of the screw, being coaxial with said longitudinal axis and having a threaded surface portion, the threaded frustums are joined to each other so that a widest end of the apical frustum is joined with a widest end of the central frustum, a narrowest end of the central frustum is joined with a narrowest end of the coronal frustum, wherein a narrowest end of the apical frustum corresponds to the lower end of the multi-frustum screw and a widest end of the coronal frustum corresponds to the upper end of the multi-frustum screw, and a tilt angle of an outer surface of each frustum with respect to the common longitudinal axis, ranges between 0.50° and 60°.

2. The screw for implants according to claim 1, wherein the tilt angle ranges from 0.5° to 20° for dentistry screws.

3. The screw for implants according to claim 1, wherein the tilt angle ranges from 1° to 10°, for dentistry screws.

4. The screw for implants according to claim 1, wherein the tilt angle of said frustums are equiangular.

5. The screw for implants according to claim 1, wherein the tilt angles of said frustums are different.

6. The screw for implants according to claim 1, wherein the average thread pitch ranges from 0.1 mm to 2.5 mm.

7. The screw for implants according to claim 6, wherein the thread pitch at the upper end of the screw is less than the thread pitch at the lower end of the screw.

8. The screw for implants according to claim 7, wherein the thread pitch at the upper end of the screw ranges between 0.1 mm and 0.5 mm, while the thread pitch at the lower end of the screw ranges between 0.3 mm and 2.5 mm.

9. The screw for implants according to claim 1, wherein a union between the narrowest end of said coronal frustum and the narrowest end of the central frustum forms a waist of the screw and a union between the widest end of said central frustum and the widest end of the apical frustum forms a greatest diameter of the screw.

10. The screw for implants according to claim 9, wherein the length of the screw measured from the upper end to the lower end is from 6 mm to 120 mm and the greatest diameter is between 2 and 10 mm.

11. The screw for implants according to claim 1, wherein said internal gap has a bottom shaped as a polygon of 6 to 12 sides and positioned adjacent to said threaded surface portion, which locks an attachment or abutment fixable in a determined position.

12. The screw for implants according to claim 11, wherein the bottom of the internal gap is shaped as a decagon.

13. The screw for implants according to claim 1, further comprising a second inner base formed by an internal gap provided on said lower end of the screw, being coaxial with said longitudinal axis and having a threaded surface portion, enabling thereby the fixation of one attachment to said upper end and another attachment to said lower end.

14. The screw for implants according to claim 1, having between 1 and 4 notches symmetrically located on the narrowest end of the apical frustum and being parallel with the axis of the screw.

15. The screw for implants according to claim 1, wherein the screw is manufactured in a material selected from the group consisting of titanium, zirconium, chrome, cobalt and alloys thereof.

16. A multi-frustum screw for dental implants comprising: four threaded frustums, the threaded frustums selected from a coronal frustum forming an upper end of the screw, an apical frustum forming a lower end of the screw, a first central frustum and a second central frustum positioned between the coronal frustum and the apical frustum, wherein the coronal frustum, the first and second central frustums, and the apical frustum have a common longitudinal axis, said screw has an inner base formed by an internal gap provided on said upper end of the screw, being coaxial with said longitudinal axis and having a threaded surface portion, the threaded frustums are joined to each other so that a widest end of the apical frustum is joined with a widest end of the first central frustum, a narrowest end of the first central frustum is joined with a narrowest end of the second central frustum and a widest end of the second central frustum is joined with a widest end of the coronal frustum, wherein a narrowest end of the apical frustum corresponds to the lower end of the multi-frustum screw and a narrowest end of the coronal frustum corresponds to the upper end of the multi-frustum screw, and a tilt angle of an outer surface of each frustum with respect to the common longitudinal axis, ranges between 0.50° and 60°.

17. The screw for implants according to claim 16, wherein the tilt angle ranges from 0.5° to 20° for dentistry screws.

18. The screw for implants according to claim 16, wherein the tilt angle ranges from 1° to 10°, for dentistry screws.

19. The screw for implants according to claim 16, wherein the tilt angle of said frustums are equiangular.

20. The screw for implants according to claim 16, wherein the tilt angles of said frustums are different.

21. The screw for implants according to claim 16, wherein the average thread pitch ranges from 0.1 mm to 2.5 mm.

22. The screw for implants according to claim 21, wherein the thread pitch at the upper end of the screw is less than the thread pitch at the lower end of the screw.

23. The screw for implants according to claim 22, wherein the thread pitch at the upper end of the screw ranges between 0.1 mm and 0.5 mm, while the thread pitch at the lower end of the screw ranges between 0.3 mm and 2.5 mm.

24. The screw for implants according to claim 16, wherein said internal gap has a bottom shaped as a polygon of 6 to 12 sides and positioned adjacent to said threaded surface portion, which locks an attachment or abutment fixable in a determined position.

25. The screw for implants according to claim 24, wherein the bottom of the internal gap is shaped as a decagon.

26. The screw for implants according to claim 16, wherein the screw is manufactured in a material selected from the group consisting of titanium, zirconium, chrome, cobalt and alloys thereof.

* * * * *